United States Patent
Adeosun et al.

(10) Patent No.: US 10,626,192 B2
(45) Date of Patent: Apr. 21, 2020

(54) PROCESS FOR REDUCING PROPYLENE CHLOROHYDRIN IN HYDROXYPROPYLATED PRODUCTS

(71) Applicant: CORN PRODUCTS DEVELOPMENT, INC., Sao Paulo (BR)

(72) Inventors: John Adeosun, Union, NJ (US); Abhay Borkar, Dayton, NJ (US); Qian Wei, Wayne, NJ (US); John Pantina, Somerset, NJ (US); Judith M. Vaz, Piscataway, NJ (US)

(73) Assignee: CORN PRODUCTS DEVELOPMENT, INC., Westchester, IL (US)

( * ) Notice: Subject to any disclaimer, the term of this patent is extended or adjusted under 35 U.S.C. 154(b) by 163 days.

(21) Appl. No.: 15/584,154

(22) Filed: May 2, 2017

(65) Prior Publication Data

US 2018/0319902 A1    Nov. 8, 2018

(51) Int. Cl.
| | |
|---|---|
| *C08B 31/00* | (2006.01) |
| *C07C 19/01* | (2006.01) |
| *C08B 31/12* | (2006.01) |
| *C01B 25/455* | (2006.01) |
| *C01B 25/12* | (2006.01) |
| *G01N 30/72* | (2006.01) |
| *C07D 303/02* | (2006.01) |

(52) U.S. Cl.
CPC .......... *C08B 31/006* (2013.01); *C07C 19/01* (2013.01); *C08B 31/12* (2013.01); *C01B 25/12* (2013.01); *C01B 25/455* (2013.01); *C07D 303/02* (2013.01); *G01N 30/7206* (2013.01)

(58) Field of Classification Search
CPC ............................. C08B 31/06; C08B 31/006
USPC .......................................................... 426/578
See application file for complete search history.

(56) References Cited

U.S. PATENT DOCUMENTS

| | | |
|---|---|---|
| 4,112,222 A | 9/1978 | Jarowenko |
| 4,431,800 A | 2/1984 | Leusner et al. |
| 4,847,371 A | 7/1989 | Schara et al. |
| 5,187,272 A | 2/1993 | Katcher et al. |
| 5,512,311 A * | 4/1996 | Capitani ................ A21D 2/186 426/578 |
| 5,851,959 A | 12/1998 | Bernu |
| 9,605,087 B1 | 3/2017 | Han |
| 2014/0148591 A1 | 5/2014 | Engleman et al. |

FOREIGN PATENT DOCUMENTS

| | | | |
|---|---|---|---|
| EP | 0796868 A2 | 9/1997 | |
| EP | 1229049 A2 | 8/2002 | |
| EP | 1339049 A2 * | 8/2003 | ........... G11B 7/1267 |
| WO | 2015/183939 A1 | 12/2015 | |

* cited by examiner

*Primary Examiner* — Jyoti Chawla
(74) *Attorney, Agent, or Firm* — Jacqueline Cohen; Jason Grauch; Rachael Casey

(57) ABSTRACT

A method of reducing the amount propylene chlorohydrin produced in a reaction to make a hydroxypropylated/crosslinked starch comprising removing residual propylene oxide from alkaline slurry. The residual propylene oxide is removed by the dewatering the alkaline slurry or by washing the starch in slurry at a pH of around 10. The starch is then neutralized in an acid solution and recovered from the second slurry and may or may not be washed, depending on whether the slurry while at pH around 10 to make a hydroxypropylated/crosslinked starch having less than 1 ppm propylene chlorohydrin.

18 Claims, 3 Drawing Sheets

PROCESS FOR REDUCING PROPYLENE CHLOROHYDRIN IN HYDROXYPROPYLATED PRODUCTS

BACKGROUND

The current invention is directed to a method for reducing the propylene chlorohydrin byproduct from reactions involving hydroxypropylated hydrocolloids. More specifically the disclosed process is capable of reducing the amount of propylene chlorohydrin to less than 1 ppm in a hydroxypropylated/crosslinked hydrocolloids, with minimal crosslink stripping.

Hydroxypropylation is a reaction used to modify hydrocolloids and starch (whether or not he starch is functionally a hydrocolloid). The base polymer is modified using propylene oxide (PO). When a crosslinking agent, such as phosphorus oxychloride ($POCl_3$), is added to the hydroxypropylated product can be referred to as hydroxypropylated/crosslinked. A product that is only subject to a crosslinking agent is referred to as crosslinked.

Hydroxypropylation and crosslinking are used to modify the functionality of the polymer. Considering starch specifically, hydroxypropylated starches are commonly used to provide viscosity and freeze-thaw stability in food products such as puddings, fruit pie fillings, sauces, salad dressings, and gravies. Hydroxypropylated/crosslinked starches further provide enhanced product texture, viscosity, and stability for processing and storage.

The process of hydroxypropylating a biopolymer, however, creates propylene chlorohydrin ("PCH"), an undesirable byproduct. By regulation of the Joint Expert Committee on Food Additives, PCH must be less than 1 ppm in modified food starches. The standard process for making hydroxypropylated/crosslinked starch yields PCH that exceeds these levels, requiring extra washing of the starch to remove the byproduct. But extensive washing increases starch losses and increases the amount of waste water to clean. So there is interest in other methods of reducing PCH.

One method, which is described in U.S. Pat. No. 4,431,800, takes advantage of the volatility of the propylene oxide, also called PO (a precursor to PCH) by aerating the starch slurry at high pH after completing the hydroxypropylation reaction. The '800 patent reports bench studies running for between 0.25 and 24 hours. At commercial scale, however, due to mixing and diffusion limitations, these times scale to become impracticable. Additionally, it is known that holding a hydroxypropylated/crosslinked starch at high pH tends to strip the crosslinking, making the method particularly unfit for reducing PCH during a process to make a hydroxypropylated/crosslinked starch.

So there is a need for a method of making a hydroxypropylated/crosslinked biopolymers that has less PCH, that uses less water and so produces less water to clean, and that does not strip the crosslinking from the starch.

SUMMARY

This specification discloses an improved method for making hydroxypropylated hydrocolloids, including hydroxypropylated and hydroxypropylated/crosslinked hydrocolloids (including starch). The method allows for making a hydroxpropylated hydrocolloid having less than 1 ppm propylene chlorohydrin, and for hydroxypropylated/crosslinked starch, allows the modified starch to be held at intermediate pH for up to at least 24 hours with minimal loss of crosslinking. An embodiment of the method comprises a) adding an acid to a slurry comprising a hydroxyproplyated or hydroxypropylated/crosslinked starch having pH greater than 11 to reduce the pH of the slurry to between 9 and 10.4; b) washing the slurry; c) neutralizing the washed slurry with acid to further reduce the pH of the slurry to less than 7.5.

In other embodiments, the method for making hydroxypropylated/crosslinked starches comprises: a) adding a starch to a mixture of water and salt to make a starch slurry; b) adding base to the starch slurry to raise the pH of the slurry to greater than 11; c) adding PO to the starch slurry to make a slurry comprising a hydroxypropylated starch; and d) adding a crosslinking agent to the slurry to make a slurry comprising a hydroxypropylated/crosslinked starch.

In other embodiments, the starch slurry can be held at pH of between 9 and 10.4 for up to 24 hours without a significant change in viscosity. In the embodiments, the viscosity of a crosslinked starch, as measured in MVU, held at pH between 9 and 10.4 for up to 24 hours is within 10% of the viscosity of similarly crosslinked starch that was neutralized following completion of the crosslinking reaction.

DETAILED DESCRIPTION

In this specification all percentages are by weight unless otherwise specified.

As used in this specification, propylene oxide may be referred to as PO.

As used in this specification, phosphorus oxychloride may be referred to as $POCl_3$.

As used in this specification, propylene chlorohydrin may be referred to as PCH.

As used in this specification, starch that is modified with both PO and a crosslinking agent (such as $POCl_3$) is referred to as a hydroxypropylated/crosslinked starch.

As used in this specification, dewatering means to remove liquid from the starch slurry to obtain a starch cake.

Figure 1:
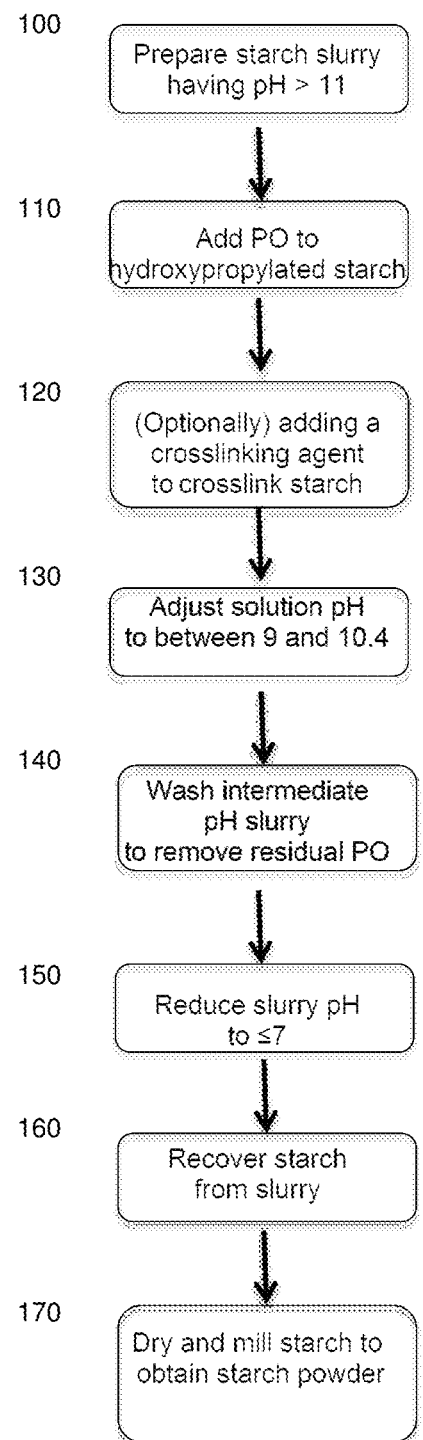
FIG. 1 is a flow chart illustrating an embodiment of the disclosed process for making hydroxypropylated/crosslinked starch with reduced PCH.

FIG. 1 is a flowchart illustrating the method for making a hydroxypropylated starch or hydroxypropylated/crosslinked starch. In alternate embodiments the method may be applied more broadly to hydrocolloids, (such as biogums). The method yields an hydroxypropylated or hydroxypropylated/crosslinked end product that contains less than 1 ppm propylene chlorohydrin. In another embodiment the method yields an end product having less than 0.5 ppm propylene chlorohydrin. In another embodiment the method yields an end product having less than 0.15 ppm propylene chlorohydrin. In another embodiment the method yields an end product having less than 0.12 ppm propylene chlorohydrin.

Step 100 starts with a with slurry comprising the base biopolymer (in embodiments a starch), water, and salt. With reference to an illustrative embodiment that modifies starch, base is added to the slurry to raise the slurry's pH to greater than 11. In step 110 propylene oxide is added to the alkaline slurry to form a hydroxypropylated starch. In step 120 a crosslinking agent, such as POCl$_3$, is optionally added to the slurry to form a hydroxypropylated/crosslinked starch. In step 130 the pH of the slurry is adjusted to be between 9 and 10.4. In step 140 the slurry is washed to remove the residual PO. In step 150 the hydroxypropylated or hydroxypropylated/crosslinked starch slurry is neutralized to a pH of 7 or less. In step 160 the hydroxypropylated or hydroxypropylated/crosslinked starch slurry is at least dewatered and dried, but may also be washed as needed. In step 170 the hydroxypropylated/crosslinked starch cake is milled to obtain the desired starch powder.

In embodiments to make a hydroxypropylated starch, the starch is first dispersed in aqueous solution. The concentration of starch to water may vary as needed, but will typically range from about 1:4 about 1:2 (w/w) starch to water. The water may be, but need not be deionized. Suitable salts may be added to the solution such as sodium carbonate, sodium chloride, or sodium sulfate. The salts are added in the range of from about 0.1% to about 20% by weight relative to the starch. In embodiments the amount of sodium sulfate is around 15%. In other embodiments the salt is between 0.5% and 5%. In other embodiments it is between about 1% and 3%. The starch slurry is reacted with propylene oxide under alkaline conditions. The amount of PO added to the slurry will range from between 0.5% to 25% by weight relative to the starch. In embodiments it will range between 3% and 15%. In other embodiments it will range between 4% and 10%. In other embodiments it will be about 5%. The PO may be added to alkaline slurry, or the pH of the slurry may be adjusted after PO is added. The pH is adjusted using suitable base, such as sodium hydroxide. Other exemplary bases include sodium carbonate, sodium citrate, tetrasodium pyrophosphate, ammonium orthophosphate, disodium orthophosphate, trisodium phosphate, calcium carbonate, calcium hydroxide, potassium carbonate, potassium hydroxide, and potassium citrate. The bases can also include any other base approved for food use under Food and Drug Administration laws or other food regulatory laws. The pH will range from between about 11 and 12, more typically about 11.5. The reaction will run until the starch has been suitable modified, typically from between 3 to 36 hours, more typically between 15 to 20 hours, and in particular embodiments for about 18 hours. The reaction will typically run at between 30° C. and 50° C., in other embodiments around 40° C. Hydroxypropylation of hydrocolloids, including gums (konjac, xanthan, guar, carageenen, gellan, modified cellulose, alginates, etc.) is done using similar principles, which those of ordinary skill can adapted to the particular polymer as needed.

Crosslinking is a reaction that creates chemical bonds among various hydroxyl groups in the starch. The bonds may through an inorganic moiety like phosphorous or may be an organic ether linkage. Numerous reactions involving bivalent and polyvalent molecules are known, and for purposes of this invention any conventional method for crosslinking a starch may be used. In preferred embodiments the reaction uses POCl$_3$. Other commonly used crosslinking agents include sodium trimetaphosphate (STMP) and mixtures of adipic and acetic anhydride. In embodiments the starch is first dispersed in aqueous solution. The concentration of starch to water may vary as needed, but will typically range from about 1:4 about 1:2 (w/w) starch to water. The water may be, but need not be deionized. Suitable salts may be added to the solution such as sodium carbonate, sodium chloride, or sodium sulfate. The salts are added in the range of from about 0.1% to about 20% by weight relative to the starch. In embodiments the amount of sodium sulfate is around 15%. In other embodiments the salt between 0.5% and 5%. In other embodiments it is between about 1% and about 3%. The POCl$_3$ is added to the solution in a range of between 0.001% and 0.05% (w/w) based on dry weight of starch. Prior to or after adding the crosslinking agent the slurry is pH adjusted to between about 11 and 12, and more typically about 11.5. Bases suitable and preferred for the reaction are the same as listed above for the hydroxypropylation reaction. The reaction is allowed to run between 15 minutes to 90 minutes, more typically from about 30 to about 60 minutes. Crosslinking reactions typically run at temperatures between 20° and 30° C. Crosslinking of hydrocolloids, including gums (konjac, xanthan, guar, carageenen, gellan, modified cellulose, alginates, etc.) is done using similar principles, which those of ordinary skill can adapted to the particular polymer as needed.

The hydroxypropylation and optional crosslinking reactions may be run sequentially in either order. In preferred embodiments the hydroxypropylation reaction is run first. The pH and salt content of the slurry need not change for the two reactions. But the temperature of the slurry must be adjusted to account for the different temperatures for hydroxypropylation reaction and crosslinking reaction.

After the modifications are completed, the pH of the solution is lowered to about 10, an intermediate pH. The slurry's pH is reduced to the intermediate pH by addition of suitable non-chloride based acid such as sulfuric acid, phosphoric acid, citric acid, acetic acid, etc. Addition of acid is controlled to precisely lower pH to avoid formation of PCH, which occurs at lower pH, and to avoid stripping the crosslinking from the starch, which occurs at high pH. The pH range is 9.0 and 10.4, preferably between 9.4 and 10.3, and more preferably between 9.8 and 10.2. The acid is added, while the slurry is being mixed, in a controlled manner over a period of time of between about 0.25 hours to 2 hours. In embodiments the acid is added over the period of 1 hour.

The starch is washed at intermediate pH by adding clean liquid (for example water) to the slurry and passing the slurry liquid through a filter. The starch may be dewatered, but preferably is not, to reduce water usage: additional liquid must be added to a dewatered starch cake to suspend the starch in slurry again. Washing can be aided with centrifugation or settling. A suitable apparatus for both dewatering and washing is described in U.S. Pat. No. 8,309,711, incorporated by reference herein. The amount of washing fluid depends on the starch base and the washing equipment, but will typically range from about 0.75:1 wash water to starch to 6:1 (w/w, starch moisture about 12%). In preferred embodiments the ratio of water to starch is close to 1:1. In embodiments it is 0.6:1. In other embodiments it is 0.7:1. Wash time may vary as needed. In embodiments the starch is washed for between about 0.5 hours and about 3 hours. Following washing the starch is neutralized by lowering the pH of the solution further to a final pH. Suitable acids include any non-chloride based acid, for example sulfuric acid, phosphoric acid, citric acid, acetic acid, etc. The pH of the starch slurry is adjusted to between about 3 and about 8. Most typically the slurry will be adjusted to a pH less than 7, and more typically between about 5 and about 7. The neutralization step is run for between about 0.25 hours and about 3 hours more typically around 1 hour. Following neutralization, the starch slurry is dewatered to form a starch cake. The starch cake is then recovered, dried, sieved, and milled to produce powder.

Figure 2:
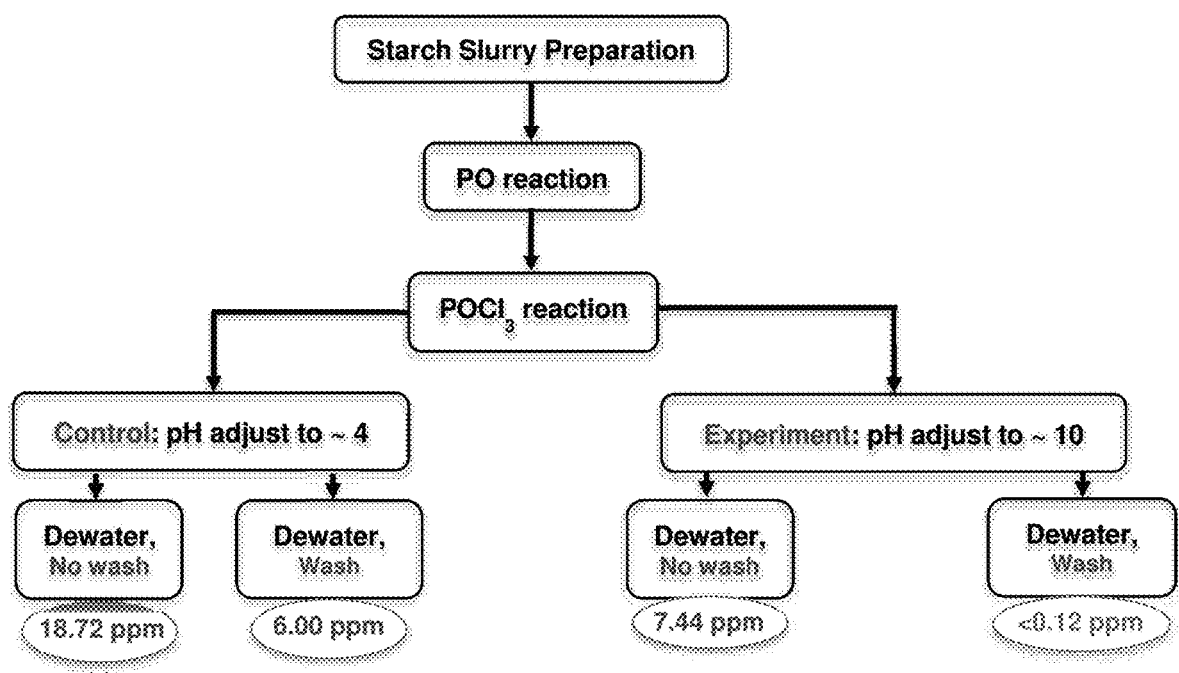
FIG. 2 is a flow chart illustrating amount of PCH obtained using various processes.

As shown in FIG. 2, by adjusting the pH of the starch solution to about 10 (as described above) and then dewatering the starch, the levels of PCH can be reduced by about 60% (18.72 ppm to 7.44 ppm). Additionally, FIG. 2 shows that by washing the starch prior to dewatering, PCH levels can be reduced to below 0.12 ppm. Without being bound by theory this results from the removal of PO before it can react with chlorine as the slurry's pH is reduced. Moreover, while again not being bound by theory, this shows that residual PO exists both in the slurry and is physically associated (not chemically bound) to the starch. It is believed that dewatering the starch removes residual PO in the slurry, but that washing at intermediate pH is needed to remove residual PO that is associated with the starch.

Figure 3:
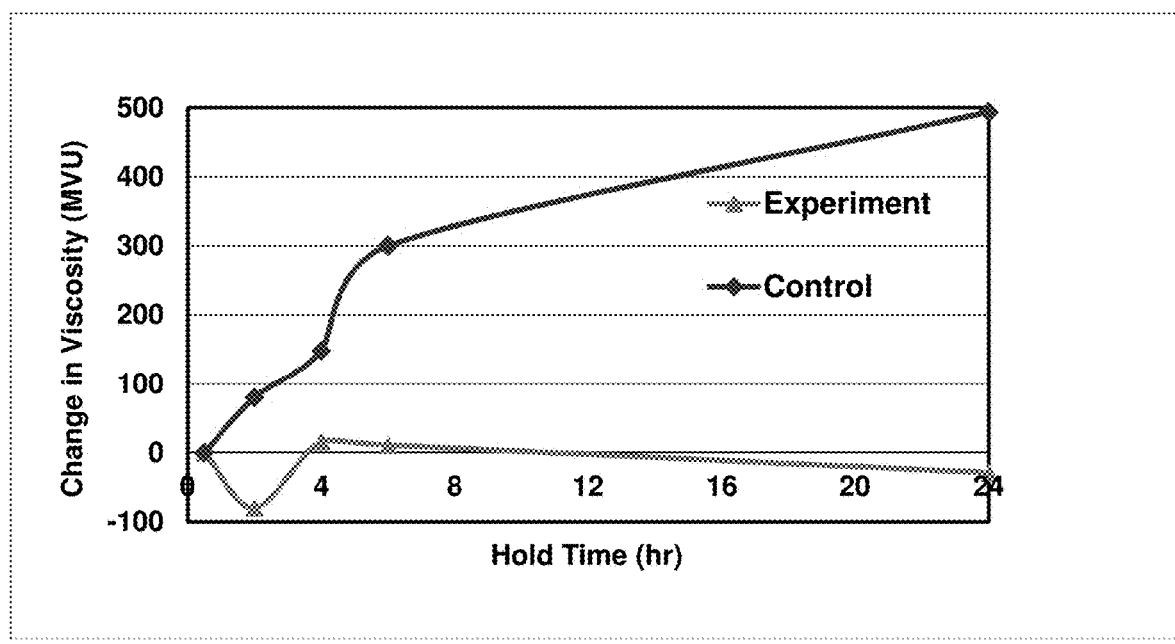
FIG. 3 is a chart depicting the change in end viscosity for (5% starch at 3 pH, heated to 95° C., held for 15 minutes) hydroxypropylated/crosslinked starch when held at pH between 9 and 10.4 and when held at pH greater than 11.

In another aspect of the invention, the starch slurry can be held at pH of about 10 for long periods of time without stripping crosslinking from the starch. In embodiments the starch can be held pH of between 9 and 10.4 for up to 24 hours with a minimal change in viscosity, as shown in FIG. 3. In embodiments the viscosity of the hydroxypropylated/crosslinked starch, as measured in MVU (5% starch at 3 pH), varies by less than 10% after 24 hours storage at pH of about 10. In other embodiments the viscosity of the hydroxypropylated/crosslinked starch, as measured in MVU (5% starch at 3 pH), varies by less than 5% after 12 hours storage at pH of about 10. Viscosity measurements were taken at the end of the following time and temperature course: the starch slurry was heated rapidly to 95° C. and held for 15 minutes, after which viscosity was recorded in Brabender Micro Visco Units (MVU).

Base starches may come from any suitable source, including but not limited to, corn, barley, wheat, rice, sorghum, waxy maize, waxy rice, waxy barley, waxy sorghum, starch obtained from pulses, cereal grains containing high amylose, potato, tapioca, high amylopectin tapioca, and the like.

The following examples are provided as illustrations and should not be construed to limit the scope of the invention in any way. Persons of ordinary skill in the art will recognize that routine modifications may be made to the methods and materials used in the examples, which would still fall within the spirit and scope of the present invention.

EXAMPLE 1

Measuring PCH Formation

Propylene chlorohydrin is measured using a gas chromatography/mass spectrometry selected ion monitoring method. The method used a GC/MS system with programmable temperature vaporization injection. A Stabilwax®-DA column was used as a stationary phase and helium was the choice of carrier gas. PCH is extracted using a methanol solvent. The PCH amounts reflect the total of two isomers of PCH detected: 1-chloro-2-propanol and 2-chloro-1-propanol.

Propylene chlorohydrin mitigation was evaluated according to the processes depicted in FIG. 2. For the control, hydroxypropylated/crosslinked starch was prepared at high pH, and without washing, was then neutralized by adjusting slurry pH to about 4. The cake was then separated into two samples one was measured for PCH content without washing, while the other was washed before measuring PCH. To show PCH control by washing at high pH washing, hydroxypropylated/crosslinked starch was prepared using standard methods. Following completion of the hydroxypropylation and crosslinking reactions, the slurry's pH was adjusted from greater than 11 to about 10 (as described below). The slurry was divided into two parts: the first portion was dewatered, but not washed; the second portion was washed and dewatered. The PCH content of both cakes was measured.

Hydroxypropylated/crosslinked starch was made as follows: 1500 g of water was measured into a reaction vessel and 250 g of sodium sulfate salt was added under agitation to the water and mixed until completely dissolved. With good agitation, 1000 g of waxy corn starch was added to the salt solution. The initial pH and temperature of the starch slurry were 5.9 and 26.1° C., respectively. The pH of the starch slurry was then raised to 11.89 (alkalinity of 66.38 mL) by adding drop-wise 500 g of 3% aqueous sodium hydroxide to the slurry. The content of the reaction vessel is transferred to PO reaction bottle, where 84 g of PO was added inside a chemical hood to the reaction bottle. The bottle was then placed on a reaction tumbler system. The PO was reacted under agitation on the tumbler for 18 hours at 40° C. After the hydroxypropylation reaction, the slurry was cooled to ambient temperature (25.6° C.) and crosslinked by adding 140 microliters of $POCl_3$ using a syringe, and allowed to react for 30 min.

In order to run the control (pH of about 4) and PCH reduction (pH of about 10) washing experiments, the slurry was divided into two weight portions of 750 g and 2642 g, respectively. For the control, 750 g slurry was put in a vessel and its pH was adjusted to 3.79 using 25% aqueous sulfuric acid. After mixing for 1 hour, the low pH slurry was spilt into two. The first 375 g slurry was just dewatered using a Buchner filter without adding wash water, while the second 375 g slurry was washed with 100 g of water and dewatered using a Buchner funnel. The final starch cake samples were sieved through a 2 mm (US 10 Mesh) screen and the sifted samples analyzed for the total PCH content.

For the PCH reduction experiment, 2642 g slurry was put in a vessel and its pH was adjusted to 9.95 (avg. alkalinity of 5.25 mL) using 25% aqueous sulfuric acid. After mixing for 1 hour, the high pH slurry was spilt roughly into two equal weights. The first 1315 g slurry was not washed while the second 1327 g slurry was washed with 300 g of water. Both were dewatered using a Buchner filter. This level of washing (on weight basis) is equal to 0.6:1 wash water to starch (~12% moisture) ratio. The final starch cake samples were sieved through a 2 mm (US 10 mesh) screen and sifted samples analyzed for their PCH content. In order to obtain the final cake samples at low pH (within 3-4) for the starch cake from both the unwashed and washed high pH slurry samples, each cake sample was reslurried by adding 1100 g each of water. The new slurries obtained from the starch cake of the unwashed and washed high pH slurry were neutralized with 25% aqueous sulfuric acid to adjust pH to 3.78 and 3.42, respectively.

The results are reported in FIG. 2. For control samples, PCH levels were measured once after neutralization for starch that had been washed or that had not been washed. Control samples that had not been washed had PCH levels of 18.72 ppm. Control samples that had been washed had PCH levels of 6.00 ppm. For test samples in which the starch slurry's pH was adjusted to 10, PCH levels were also measured for unwashed and washed cake. The unwashed samples had PCH levels of 7.44 ppm while the samples that were washed had PCH levels of less than 0.12 ppm. This shows that by washing slurry at intermediate pH of about 10, sufficient PO can be removed so that starch end product has less than 0.12 ppm PCH. This can be done using less water than is necessary to achieve similar levels of PCH by washing after the PCH formed (as the slurry's pH is lowered).

EXAMPLE 2

Avoidance of POCl₃ Stripping

Experiments were performed to study the effect of hold time (up to 24 hr.) on $POCl_3$ stripping after pH drop (from greater than 11 to approximately 10). To make salt/starch slurry, 625 g of sodium sulfate and 2500 g of waxy starch (Amioca®) were added to 3750 mL of water. 37.5 g sodium hydroxide was then added to adjust the slurry pH to about 11. The slurry was crosslinked by reacting with $POCl_3$ for 30 minutes at 95° F. A sample of crosslinked starch was collected immediately after the reactions were completed—i.e. having zero hold time. The remaining starch slurry was divided into two portions. For the experimental sample, the pH was dropped to 9.7, while the control sample was held at a higher pH of 11.7. Both the control and experimental samples were then held at a high pH for 2, 4, 6, and 24 hours. Samples were then neutralized, washed, dewatered and dried.

Crosslink stripping was measured by testing the viscosity of samples. Viscosity was measured after it is dispersed in water and gelatinized by Brabender® Micro Visco-Amylo-Graph® (manufactured by Brabender® GmbH & Co. KG, Duisburg, Germany).

Unless otherwise stated, the following paste viscosity procedure was used for all samples. Samples were slurried in a sufficient amount of distilled water to give 5% solids (w/w). The pH was adjusted to pH 3.0 with a sodium phosphate, citric acid buffer and the slurry was introduced to the sample cup of a Brabender® Micro Visco-Amylo-Graph® fitted with a 350 cm/gram cartridge. The starch slurry was heated rapidly to 95° C. and held for 15 minutes, after which viscosity was recorded in Brabender Micro Visco Units (MVU).

As shown in FIG. 3, viscosity of the starch held at about pH 10 exhibited less than 10%, viscosity change over the time period studied showing that minimal crosslink stripping occurred. For starch held at least pH 11 the viscosity increased up to 500 MVU with the hold time showing significant crosslink stripping. This shows that the disclosed method, both reduces PCH levels, but does so in a manner that protects the crosslinking within the starch.

What is claimed is:

1. A method of making a hydroxypropylated/phosphate-crosslinked starch having a propylene chlorohydrin level of less than 1 ppm comprising:
   a) obtaining an aqueous slurry having pH greater than 11 and a hydroxypropylated-phosphate-crosslinked starch by reacting in either order propylene oxide and phosphorous oxychloride with a starch;
   b) adding an acid to the slurry to reduce the pH of the slurry from greater than 11 to between about 9.0 and about 10.4;
   c) washing the slurry with a washing liquid at the pH between about 9.0 and about 10.4 to wash the hydroxypropylated/phosphate-crosslinked; and
   d) neutralizing the washed hydroxypropylated/phosphate-crosslinked starch with sufficient acid to further reduce the pH of the slurry to less than 7.5.

2. The method of claim 1 wherein the pH of step b) is reduced to between 9.4 and 10.3.

3. The method of claim 1 wherein the pH of step b) is reduced to between 9.8 and 10.2.

4. The method of claim 1 wherein the washing liquid is added to the slurry in a ratio of between about 0.75:1 to about 6:1 by weight of liquid to starch.

5. The method of claim 1 wherein the washing liquid is added to the slurry in amount of between about 0.8:1 and about 1:1 by weight of liquid to starch.

6. The method of claim 1 wherein the pH is lowered from greater than 11 to between 9 and 10.4 over the period of about 1 hour.

7. The method of claim 1 wherein the acid used in steps b) and d) does not comprise chloride ions.

8. The method of claim 1 wherein the hydroxypropylated/phosphate-crosslinked starch is held in at pH of between 9.0 and 10.4 for between 1 and 24 hours.

9. A method of reducing the amount of propylene chlorohydrin produced in a reaction to make a hydroxypropylated or hydroxypropylated/crosslinked starch comprising:
   a) mixing starch, water, and salt to make starch slurry;
   b) adding sufficient base to the starch slurry to raise the pH of the slurry to greater than 11
   c) adding a propylene oxide to the starch slurry to form a hydroxypropylated starch slurry;
   d) optionally adding a crosslinking agent to the hydroxypropylated starch slurry to form a hydroxypropylated/crosslinked starch slurry;
   e) adding an acid that does not comprise chloride ions to the hydroxypropylated or hydroxypropylated/crosslinked starch slurry in an amount sufficient to reduce the pH of hydroxypropylated or hydroxypropylated/crosslinked starch slurry to between 9.0 and 10.4;
   f) washing the starch in the hydroxypropylated or hydroxypropylated/crosslinked starch slurry in water in amount of 0.8 to 1:1 by weight of the starch;
   g) neutralizing the washed starch with sufficient acid to further reduce the pH of the slurry to less than 7.5;
   h) dewatering the slurry to recover the hydroxypropylated or hydroxypropylated/crosslinked starch.

10. A method of making a hydroxypropylated/phosphate-crosslinked starch having a propylene chlorohydrin level of less than 1 ppm comprising:
    a) obtaining an aqueous slurry having pH greater than 11 and a hydroxypropylated-phosphate-crosslinked starch by reacting in either order propylene oxide and phosphorous oxychloride with a starch;
    b) adding an acid to the slurry the pH of the slurry from greater than about 11 to between about 9.0 and about 10.4;
    b) dewatering the slurry to form hydroxypropylated/phosphate-crosslinked starch cake;
    c) suspending the hydroxypropylated/phosphate-crosslinked starch cake in a liquid to form a second starch slurry;
    d) in either order washing the second starch slurry and adding sufficient acid to the second slurry to reduce its pH to less than 7.5.

11. The method of claim 10 wherein the pH of step b) is reduced to between 9.4 and 10.3.

12. The method of claim 10 wherein the pH of step b) is reduced to between 9.8 and 10.2.

13. The method of claim 10 wherein the pH is lowered from greater than 11 to between 9 and 10.4 over the period of about 1 hour.

14. The method of claim 10 wherein the acid used in steps b) and d) does not comprise chloride ions.

15. The method of claim 10 wherein the hydroxypropylated/phosphate-crosslinked starch is held in at pH of between 9.0 and 10.4 for between 1 and 24 hours.

16. The method of claim 10 wherein the hydroxypropylated/phosphate-crosslinked starch cake is held at pH of between 9.0 and 10.4 for between 1 and 24 hours before being suspended to form the second slurry.

17. The method of claim 10 wherein the second slurry is held for between 1 and 24 hours before adding the acid in step d).

18. A method of making a hydroxypropylated hydrocolloid having a propylene chlorohydrin level of less than 1 ppm comprising:
   a) adding an acid that does not comprise chloride ions to a slurry comprising a hydroxypropylated starch having pH greater than 11 to reduce the pH of the slurry to between about 9.0 and about 10.4;
   b) washing the slurry with a washing liquid;
   c) neutralizing the washed starch with sufficient acid to further reduce the pH of the slurry to less than 7.5.

* * * * *